(12) United States Patent
Hauger et al.

(10) Patent No.: US 9,662,010 B2
(45) Date of Patent: May 30, 2017

(54) OPTICAL SYSTEM, COMPRISING A MICROSCOPY SYSTEM AND AN OCT SYSTEM

(71) Applicant: Carl Zeiss Meditec AG, Jena (DE)

(72) Inventors: Christoph Hauger, Aalen (DE); Artur Högele, Oberkochen (DE)

(73) Assignee: CARL ZEISS MEDITEC AG, Jena (DE)

(*) Notice: Subject to any disclaimer, the term of this patent is extended or adjusted under 35 U.S.C. 154(b) by 0 days.

(21) Appl. No.: 14/859,700

(22) Filed: Sep. 21, 2015

(65) Prior Publication Data
US 2016/0081545 A1 Mar. 24, 2016

(30) Foreign Application Priority Data
Sep. 19, 2014 (DE) .................. 10 2014 014 182

(51) Int. Cl.
*A61B 3/10* (2006.01)
*A61B 3/00* (2006.01)
(Continued)

(52) U.S. Cl.
CPC .......... *A61B 3/102* (2013.01); *A61B 3/1225* (2013.01); *A61B 3/13* (2013.01); *G01B 9/0203* (2013.01);
(Continued)

(58) Field of Classification Search
USPC ................................................ 351/200–246
See application file for complete search history.

(56) References Cited

U.S. PATENT DOCUMENTS

| 5,077,622 A * | 12/1991 | Lynch ................ G02B 27/64 359/557 |
| 5,321,501 A | 6/1994 | Swanson et al. |

(Continued)

FOREIGN PATENT DOCUMENTS

| DE | 10 2005 031 496 A1 | 1/2007 |
| DE | 10 2007 019 677 A1 | 5/2008 |

(Continued)

OTHER PUBLICATIONS

Extended European Search Report in corresponding European Application No. EP 15 00 2723 dated Feb. 10, 2016.
(Continued)

*Primary Examiner* — Mohammed Hasan
(74) *Attorney, Agent, or Firm* — Patent Portfolio Builders PLLC

(57) ABSTRACT

The disclosure relates to an optical system for inspecting an eye, having an OCT system which is configured to generate a measurement beam, which is incident on an object region in a converging manner to form a measurement focus. The OCT system has a beam expander which is disposed along the measurement beam between the scanning system and the objective lens and generates an intermediate focus between the scanning system and the objective lens. The OCT system is configured to generate different values of a beam waist diameter of the beam waist by means of controlling the controllable beam expansion of the beam expander. At the different values of the beam waist diameter, an axial beam waist position of the beam waist is substantially identical.

24 Claims, 7 Drawing Sheets

(51) Int. Cl.
  *A61B 3/12* (2006.01)
  *A61B 3/13* (2006.01)
  *G01B 9/02* (2006.01)
  *G02B 21/02* (2006.01)
  *G02B 27/09* (2006.01)

(52) U.S. Cl.
  CPC ..... *G01B 9/02035* (2013.01); *G01B 9/02091* (2013.01); *G02B 21/025* (2013.01); *G02B 27/095* (2013.01)

(56) References Cited

U.S. PATENT DOCUMENTS

| | | | |
|---|---|---|---|
| 5,359,417 | A | 10/1994 | Müller et al. |
| 5,493,109 | A | 2/1996 | Wei et al. |
| 5,506,634 | A | 4/1996 | Wei et al. |
| 5,615,038 | A * | 3/1997 | Suzuki ............... G02B 26/127 250/235 |
| 5,657,128 | A | 8/1997 | Müller et al. |
| 5,795,295 | A | 8/1998 | Hellmuth et al. |
| 5,975,699 | A | 11/1999 | Hellmuth |
| 5,991,090 | A | 11/1999 | Strähle |
| 6,004,314 | A | 12/1999 | Wei et al. |
| 6,095,648 | A | 8/2000 | Birngruber et al. |
| 6,212,006 | B1 | 4/2001 | Reiner |
| 6,377,349 | B1 | 4/2002 | Fercher |
| 6,409,345 | B1 | 6/2002 | Molebny et al. |
| 6,550,917 | B1 | 4/2003 | Neal et al. |
| 6,736,510 | B1 | 5/2004 | Van Heugten |
| 7,022,117 | B1 | 4/2006 | Hohla et al. |
| 7,036,934 | B1 | 5/2006 | Youssefi et al. |
| 7,241,012 | B2 | 7/2007 | Mihashi et al. |
| 7,488,070 | B2 | 2/2009 | Hauger et al. |
| 7,692,797 | B2 | 4/2010 | Kawahara |
| 7,699,468 | B2 | 4/2010 | Gaida |
| 7,761,139 | B2 | 7/2010 | Tearney et al. |
| 7,823,782 | B2 | 11/2010 | Yatagai et al. |
| 7,839,494 | B2 | 11/2010 | Reimer et al. |
| 7,889,423 | B2 | 2/2011 | Reimer et al. |
| 2001/0036002 | A1 | 11/2001 | Tearney et al. |
| 2003/0160942 | A1 | 8/2003 | Xie et al. |
| 2003/0193647 | A1 | 10/2003 | Neal et al. |
| 2004/0012760 | A1 | 1/2004 | Mihashi et al. |
| 2005/0241653 | A1 | 11/2005 | Van Heugten et al. |
| 2005/0243276 | A1 | 11/2005 | Van Heugten et al. |
| 2006/0066869 | A1 | 3/2006 | Ueno et al. |
| 2006/0114411 | A1 | 6/2006 | Wei et al. |
| 2006/0152677 | A1 | 7/2006 | Youssefi et al. |
| 2007/0013918 | A1 | 1/2007 | Hauger et al. |
| 2007/0046948 | A1 | 3/2007 | Podoleanu et al. |
| 2007/0229760 | A1 | 10/2007 | Hirohara et al. |
| 2008/0117432 | A1 | 5/2008 | Reimer et al. |
| 2008/0117503 | A1 | 5/2008 | Reimer et al. |
| 2008/0117504 | A1 | 5/2008 | Reimer et al. |
| 2008/0186551 | A1 | 8/2008 | Hanft et al. |
| 2008/0304144 | A1 | 12/2008 | Reimer et al. |
| 2009/0279052 | A1 | 11/2009 | Hauger et al. |
| 2010/0014156 | A1 | 1/2010 | Iketaki |
| 2010/0033676 | A1 | 2/2010 | De Vries et al. |
| 2011/0026035 | A1 | 2/2011 | Muto et al. |
| 2011/0228218 | A1 | 9/2011 | Hauger et al. |
| 2012/0002274 | A1 * | 1/2012 | Knoblich ............... G02B 21/24 359/380 |
| 2012/0092615 | A1 | 4/2012 | Izatt et al. |
| 2013/0141695 | A1 | 6/2013 | Buckland et al. |
| 2013/0265545 | A1 | 10/2013 | Buckland et al. |

FOREIGN PATENT DOCUMENTS

| | | |
|---|---|---|
| DE | 10 2007 019 678 A1 | 5/2008 |
| DE | 10 2007 019 679 A1 | 5/2008 |
| DE | 10 2007 019 680 A1 | 5/2008 |
| DE | 10 2008 059 876 A1 | 6/2010 |
| DE | 10 2011 119 899 A1 | 6/2013 |
| EP | 1 918 753 A1 | 5/2008 |
| WO | 2010/060622 A2 | 6/2010 |

OTHER PUBLICATIONS

Office Action in related German Application No. DE 10 2014 014 182.9 dated Jun. 12, 2015.

HAAS Laser Technologies; "25mm Catalog, Copyright 2009"; [downloaded at http://www.haaslti.com/specialty-catalogs/25mm-Series-Catalog.pdf on Dec. 21, 2015.]; pp. 1-46.

* cited by examiner

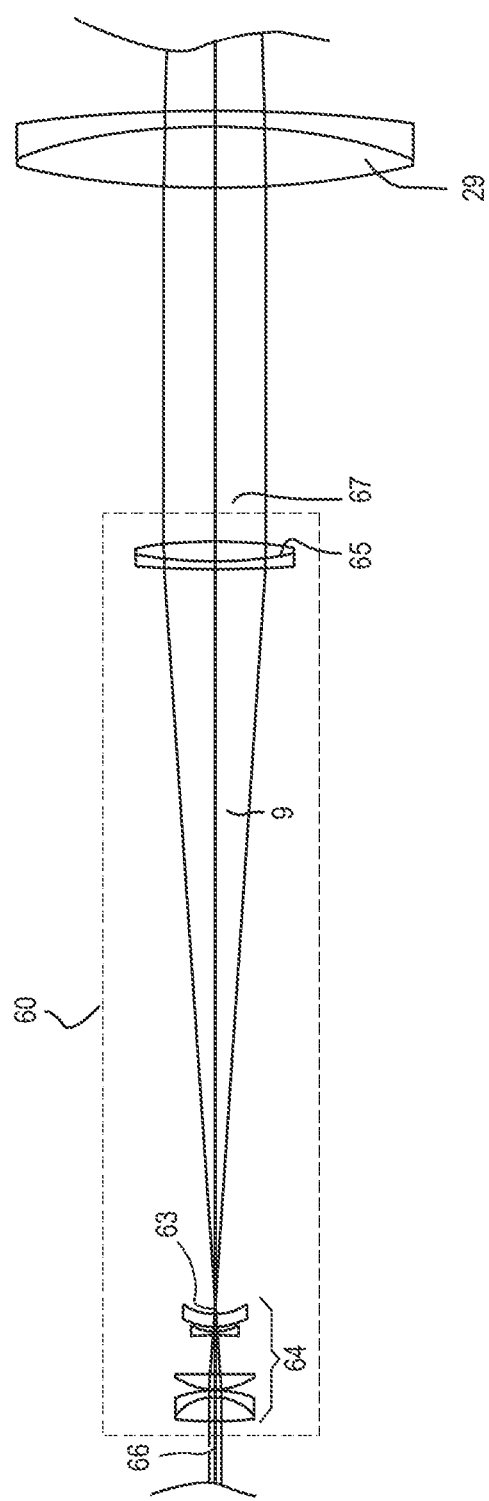

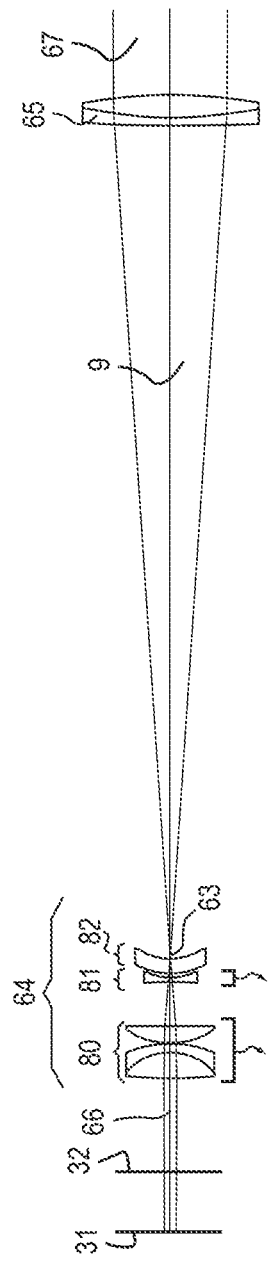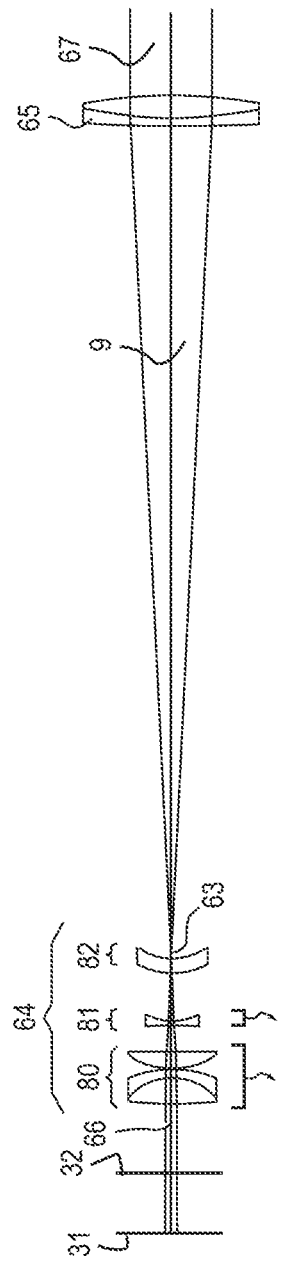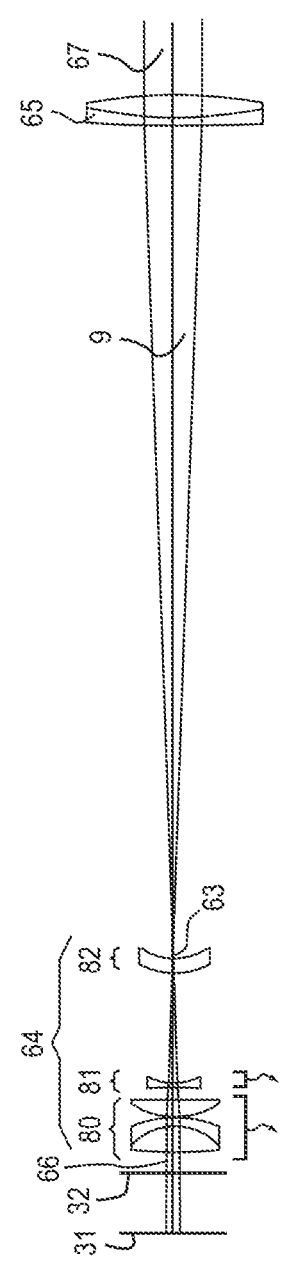

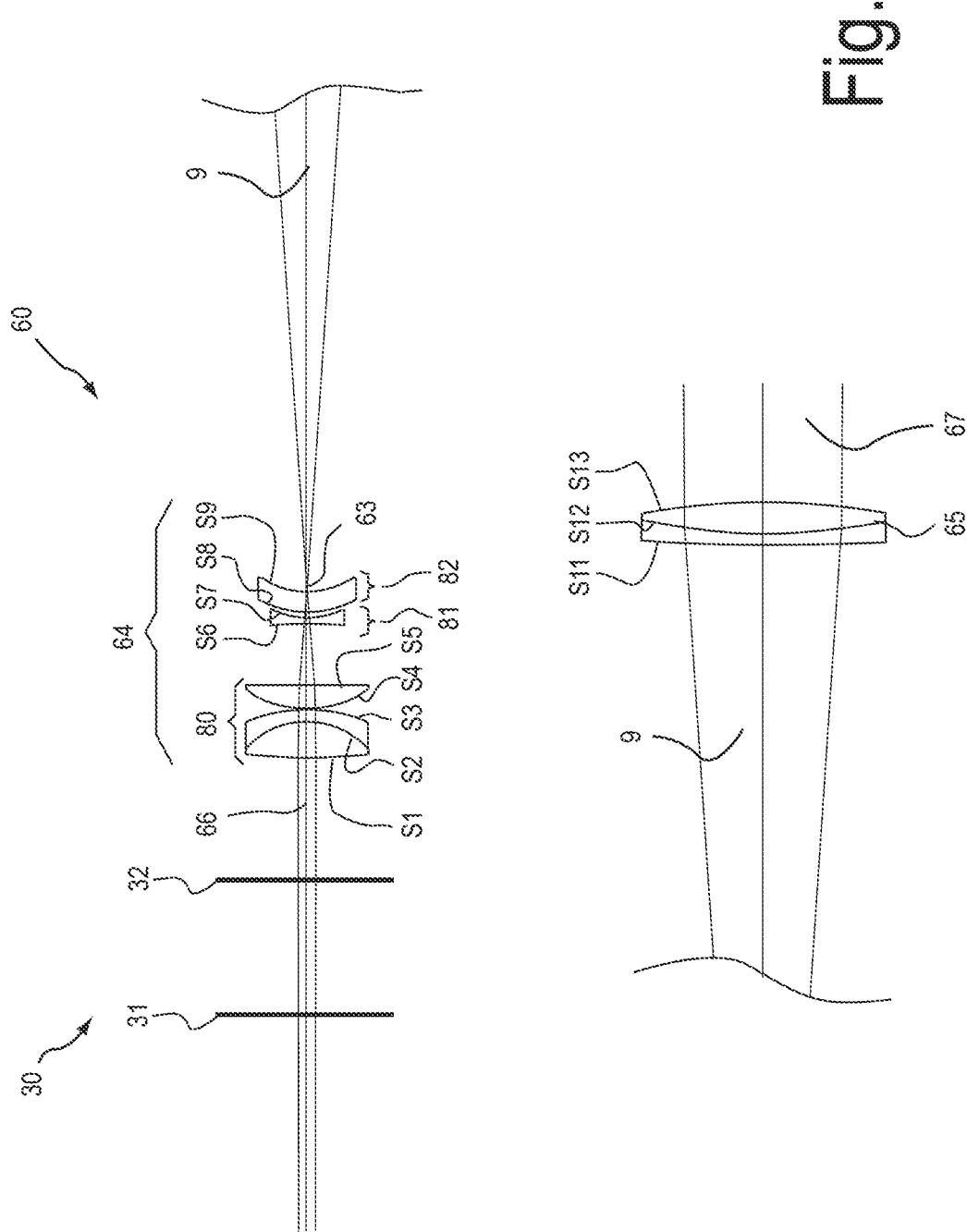

OPTICAL SYSTEM, COMPRISING A MICROSCOPY SYSTEM AND AN OCT SYSTEM

CROSS-REFERENCES TO RELATED APPLICATIONS

The present application claims priority of Patent Application No. 10 2014 014 182.9, filed on Sep. 19, 2014 in Germany, the entire contents of which are incorporated herein by reference.

FIELD

The present disclosure relates to an optical system, which includes an OCT system and which is configured to control a beam waist diameter of the OCT beam. Specifically, the present disclosure relates to an optical system which includes a microscopy system and an OCT system and which allows coupled and/or decoupled control of operational parameters, such as the beam waist diameter.

BACKGROUND

Optical coherence tomography (OCT) has become an important non-invasive diagnostic technique for the eye. In an increasing manner, this technique is also utilized intraoperatively. OCT allows generation of cross-sectional or volume images of the anterior or posterior section of the eye at a comparatively high resolution and almost in real-time.

One example for the frequent application of OCT for the posterior section of the eye is diagnosis of glaucoma, changes in the macula as well as diseases of the retina. In the anterior section of the eye, OCT is, for example, applied for pre-, intra- and postoperative diagnosis during cataract surgeries.

The numerous applications for using OCT systems have led to the development of optical systems, which combine microscopy systems and OCT systems. Such systems allow OCT analysis in the visual field of the microscopy system so that the surgeon can adjust the OCT scanning region by using the microscopy system. The generated OCT images can improve intraoperative orientation and diagnosis for the surgeon and thereby ensure an optimal surgery.

However, it has been shown that these systems are difficult to operate during surgical procedures. In particular, it has been shown that using these systems intraoperatively poses different requirements for the controller and the user interface, compared to using these systems for purely diagnostic measurements.

However, easy and efficient operability is an important factor for the surgeon in order to use OCT during surgical procedures in a beneficial manner.

Therefore, a need exists for improved OCT systems, which allow efficient use during eye surgeries.

SUMMARY

Embodiments provide optical system for inspecting an eye, the optical system comprising: a microscopy system for generating an image of an object region in an image plane. The optical system may comprise an OCT system, which is configured to acquire OCT image data, wherein the OCT system generates a measurement beam, which is incident on the object region in a converging manner to form a measurement focus. The optical system may further comprise a user interface, which is selectively switchable into a coupled operating mode and into a decoupled operating mode. In the coupled operating mode, an adjustment of a first operating parameter and an adjustment of a second parameter may be limited to a predefined dependency between the first and the second operating parameters. In the decoupled operating mode, the first and the second operating parameters may be adjustable independently from the predefined dependency. The acquired OCT image data may depend on the first operating parameter and the image which is generated in the image plane depends on the second operating parameter.

Thereby, an optical system is provided, which allows efficient use of an OCT system during a medical examination or during a surgery.

The microscopy system may be configured or may be configurable for imaging an object region of an anterior section of the eye and/or an object region of a posterior section of the eye. The optical system may have two operating modes. A first operating mode may be configured for imaging an object region of the anterior section of the eye. A second operating mode may be configured for imaging an object region of a posterior section of the eye. The anterior section may include the cornea, the natural lens and the iris. The posterior section may include the vitreous body and the fundus, in particular the retina.

The image plane of the microscopy system may be optically conjugate to an object plane. The object region may be located in the object plane. The microscopy system may include imaging optics. The imaging optics may be configured so that the object region is imaged onto the image plane by the imaging optics. Thereby, it is possible to image a portion of the anterior section of the eye.

The imaging optics may be switchable to a second configuration, in which an object region of the posterior section of the eye is imageable onto the image plane. The imaging may be performed by using the eye. In other words, in the second configuration, the object plane is optically conjugate with the image plane by virtue of an optical system, which includes the eye.

The microscopy system may be a monoscopic or a stereoscopic microscopy system. The microscopy system may include one or more observation channels. The microscopy system may include two stereoscopic observation channels. Each of the observation channels may form an image of the object region in a respective image plane. The axes of the stereoscopic observation channels may intersect at a stereo angle. The stereo angle may be between 5 degrees and 20 degrees or between 10 degrees and 16 degrees.

The optical system may include an objective lens. One or more observation channels of the microscopy system may traverse the objective lens. Alternatively or additionally, the measurement beam of the OCT system may traverse the objective lens. The measurement beam may traverse the objective lens along or substantially along the optical axis of the objective lens. The observation channels may traverse the objective lens at a distance from the optical axis of the objective lens. The objective lens may have a focal length which is greater than 100 mm, or greater than 150 mm, or greater than 200 mm. The focal length of the objective lens may be less than 500 mm, less than 400 mm, or less than 350 mm.

The OCT system may be a time domain OCT system (TD-OCT), and/or a frequency domain OCT system (FD-OCT). The OCT system may be a spectral domain OCT system (SD-OCT) and/or a swept source OCT system (SS-OCT).

The OCT system may generate the measurement beam and a reference beam. The OCT system may be configured to cause the measurement beam and the reference beam to interfere. The OCT system may configured so that the measurement beam is guided to the object region. The measurement beam may pass through the object plane. A section of the measurement beam may extend within a light guide. The light guide may be an optical fiber. The optical fiber may be a multimode fiber and/or a monomode fiber.

The OCT system may include measurement beam optics. The measurement beam optics may be an imaging optical system. The measurement beam optics may image a light entrance into a focus. The focus may be the measurement focus. The measurement focus may be arrangeable in the anterior section of the eye. Alternatively, the focus may be imaged into the measurement focus by using the eye and an ancillary ophthalmoscopy module. The ancillary ophthalmoscopy module may include a plurality of optically effective surfaces. The eye may focus a section of the measurement beam, which emerges from the ancillary ophthalmoscopy module, within the posterior section by the eye. Thereby, it is possible to arrange the measurement focus within the posterior section of the eye.

The light entrance, which is imaged by the measurement beam optics into the focus may be the entrance of the measurement beam into the measurement beam optics. The light entrance may be a transition between a non-imaging optical system (such as an optical fiber) and the imaging measurement beam optics. The light entrance may be a light exit surface of a light guide.

The measurement beam optics may include a scanning system, which is configured for one-dimensional or two-dimensional lateral scanning of the measurement focus. In other words, the scanning system may be configured to scan the measurement beam in a scanning plane of the measurement focus. The scanning plane may be oriented perpendicular to an axis of the measurement beam. The scanning system may include one or two deflecting elements. A deflecting element may be a reflective optical element, such as a mirror. The deflecting element may be pivotably mounted.

The measurement focus may be located in an axial measurement range of the OCT system. The axial measurement range may be defined as an axial range along an axis of the measurement beam, over which a data of scattering intensities are acquirable by the OCT system. The acquiring of the data may be performed by an axial scan. At least a portion of the axial measurement range may be located in the object region.

The user interface may include one or more control elements. A control element may be implemented through a graphical user interface or may be an electro-mechanical control element, such as a switch and/or a control. Each of the control elements can be selectively put into one of a plurality of states. In the coupled operating mode, a state of a first control element may be coupled to a state of a second control element. The controller may be configured to adjust the first operating parameter depending on the state of the first control element and to adjust the second operating parameter depending on the state of the second control element. In other words, for each of the control elements, there may exist a predefined dependency between the state of the respective control element and the value of the corresponding operating parameter. In the decoupled operating mode, by using the control elements, the first and the second operating parameters are adjustable independently from the predefined dependency between the first and the second operating parameters. In other words, the first and the second operating parameters are adjustable so that they do not satisfy the predefined dependency between the first and the second operating parameters.

The optical system may be configured so that the predefined dependency between the first and the second operating parameters is configurable via the user interface, in particular via the graphical user interface. The optical system may include a data storage, which is configured to store the data, which represent the predefined dependency. In order to perform the coupled operation, the controller may be configured to read the data and to control the user interface so that the adjustment of the first and the second control element is limited to the predefined dependency.

According to an embodiment, the microscopy system includes a zoom system for varying a magnification of the generation of the image through varying a zoom magnification of the zoom system. The first operating parameter may be the zoom magnification or may depend on the zoom magnification. Alternatively or additionally, the second operating parameter may be a beam waist diameter of a beam waist of the measurement beam, or may depend on the beam waist diameter.

The zoom system may be disposed in the imaging beam path of the microscopy system which is used for the image generation in the image plane. The zoom system may be disposed in the imaging beam path downstream of the objective lens. The zoom system may consist of two subsystems, wherein each of the subsystems is traversed by a separate observation channel. The zoom system may be an afocal system or substantially an afocal zoom system. The measurement beam may extend outside of the zoom system.

The beam waist diameter may be a diameter of a beam waist. The beam waist may be defined as a position within the measurement focus at which the diameter of the measurement beam has a minimum value. In other words, the beam waist may be defined as a location within the measurement focus, where the measurement beam has its narrowest constriction. The beam waist may be within the axial measurement range of the OCT system.

According to a further embodiment, an object region is located in an object plane which is optically conjugate to an image plane. The first operating parameter may be the object plane distance or may depend on the object plane distance. Alternatively or additionally, the second operating parameter may be an axial beam waist position of a beam waist of the measurement focus, or may depend on the axial beam waist position.

The object plane distance may be defined as a distance between a stationary component of the imaging optics of the microscopy system and the object plane. The stationary component may be a component, which is immovable relative to the microscope system. By way of example, the object plane distance may be a distance between the objective lens of the microscope system and the object plane. In other words, the object plane distance may be measured relative to a stationary reference point. The object plane distance may be measured, for example, along an optical axis of the imaging optics. The axial beam waist position may be an axial position of the beam waist relative to an axis of the measurement beam. The axial position of the beam waist may be defined relative to a stationary reference point.

According to a further embodiment, in the coupled operating mode, an adjustment of a third operating parameter and an adjustment of a fourth operating parameter is limited to a predefined dependency between the third and the fourth operating parameters. In the decoupled operating mode, the third and the fourth operating parameters may be adjustable independently from the predefined dependency. The first operating parameter may be the zoom magnification or may dependent on the zoom magnification. The second operating parameter may be the diameter of the beam waist or may depend on the diameter of the beam waist. The third operating parameter may be the object plane distance or may depend on the object plane distance. The fourth operating parameter may be the axial beam waist position or may depend on the axial beam waist position.

According to an embodiment, the user interface is configured so that a desired distance between the object plane and a beam waist of the measurement focus is inputtable by a user input. The user interface may be configured for selection, whether at the desired distance: either a value of an object plane distance of the object plane is identical or substantially identical to a value of the object plane distance when the desired distance (d) is input; or whether a value of an axial beam waist position of the beam waist is identical or substantially identical to a value of the axial beam waist position, when the desired distance (d) is input. The desired distance may be measured along an optical axis of the microscope system and/or along an axis of the measurement beam.

Therefore, a change in the distance can achieved so that at the changed distance, selectively either the axial beam waist position or the object plane distance has the value before the change of the distance.

The user interface may include a control element for inputting by a user the desired distance between the object plane and the beam waist of the measurement focus. The controller of the optical system may bef configured so that depending on the user's input via the user interface, the desired distance is adjusted either so that (a) the value of the object plane distance of the object plane at the desired distance is identical or substantially identical to a value of the object plane distance when the desired distance is input via the graphical user interface; or that (b) the value of the axial position of the beam waist at the desired distance is identical or substantially identical to the value of the axial beam waist position when the desired distance is input.

According to a further embodiment, the optical system comprises a controller for controlling a beam waist diameter of a beam waist of the measurement focus and for controlling the zoom magnification. The controller may be configured for a coupled control of the beam waist diameter and the zoom magnification according a predefined dependency between the beam waist diameter and the zoom magnification. The controller may be configured for selectively activating and deactivating the coupled control of the beam waist diameter and the zoom magnification.

The measurement beam optics may include one or more controllably movable optical units, which are movable depending on signals of the controller. By means of a movement of the movable optical units, the beam waist diameter may be adjustable.

When the coupled control is deactivated, the beam waist diameter and the zoom magnification are adjustable so that the predefined dependency is not satisfied.

According to a further embodiment, the controller is further configured for a coupled control of the beam waist diameter and a length of an axial measurement range of the OCT system. According to a predefined dependency between the beam waist diameter and the length of the axial measurement range. The coupled control may be performed according to a predefined dependency between the beam waist diameter and the length of the axial measurement range.

The predefined dependency may be configured so that a maximum diameter of the measurement beam within the axial measurement ranges is smaller than a predefined maximum beam diameter. The predefined maximum beam diameter may therefore represent a minimum value for desired lateral resolution within the axial measurement range. The predefined dependency may be configured so that the diameter of the measurement beam at the limits of the measurement range has the predefined maximum beam diameter.

Embodiments provide an optical system for inspecting an eye, the optical system comprising: an OCT system which is configured to generate a measurement beam, which is incident on an object region in a converging manner to form a measurement focus which comprises a beam waist. The OCT system may comprise a scanning system, an objective lens, and a beam expander, wherein the beam expander may be configured for a controllable beam expansion of the measurement beam. The scanning system, the objective lens and the beam expander may be disposed in the measurement beam. The beam expander may be disposed along the measurement beam between the scanning system and the objective lens. The beam expander may generate an intermediate focus between the scanning system and the objective lens. The OCT system may be configured to generate different values of a beam waist diameter of the beam waist by means of controlling the controllable beam expansion. At the different values of the beam waist diameter, an axial beam waist position of the beam waist may be identical or substantially identical.

The beam expander may be in signal communication with a controller. The beam diameter of a section of the measurement beam, which emerges from the beam expander may be greater than 1.5 times or greater than 2 times a diameter of a section of the measurement beam, which is incident on the beam expander. The beam diameter of the section of the measurement beam, which emerges from the beam expander may be smaller than 50 times or smaller than 20 times a diameter of a section of the measurement beam which is incident on the beam expander. At the different values of the beam waist diameter, the section of the measurement beam, which emerges from the beam expander and/or the section of the measurement beam, which is incident on the beam expander may be divergent, convergent, parallel or substantially parallel.

The OCT system may include an objective lens. The objective lens may be disposed between the beam expander and the measurement focus.

At the different values of the beam waist diameter, the measurement beam may have different values of a numerical aperture at the measurement focus. A ratio of a maximum value of the numerical aperture over a minimum value of the numerical aperture may be greater than 1.5, or greater than 1.7, or greater than 1.8. The ratio may be smaller than 10 or smaller than 5.

According to a further embodiment, at each of the different values of the beam waist diameter, a position of an object-side focal plane of the beam expander is identical or substantially identical. The object-side focal plane may be generated by all optically effective surfaces of the beam expander. Optically effective surfaces may be for example refractive or reflective surfaces. The position of the object-side focal plane may be measured along the optical axis of the beam expander, along the axis of the measurement beam and/or relative to a stationary reference point. Alternatively, at each of the different values of the beam waist diameter, the beam expander may be an afocal system or substantially an afocal system.

According to a further embodiment, the optical system comprises a microscopy system, which is configured for generating an image of an object region in an image plane. The object region may be located in an object plane, which is optically conjugate to the image plane. The microscope system may be configured to generate an observation channel for generating the image, wherein the observation channel traverses the objective lens. At the different values of the beam waist diameter, the beam waist may be located outside of the object plane. In other words, the beam waist may be located at a distance from the object plane, wherein the distance is measured along the optical axis of the microscope system or measured along the axis of the measurement beam. The object plane may be located in a focal plane of the objective lens.

According to a further embodiment, a focal length of the beam expander, which is generated by a portion or by all optically effective surfaces of the beam expander, is controllably variable. The optically effective surfaces, which generate the variable focal length, may focus the section of the measurement beam, which is incident on the beam expander into the intermediate focus.

The variable focal length may be defined as the distance between a focus or between the intermediate focus and a principal plane of those optically effective surfaces of the beam expander, which generate the variable focal length, wherein the section of the beam, which is incident on the optically effective surfaces is parallel and has a light path which is directed toward the object. The variable focal length may be an object-side focal relative to those optically effective surfaces, which generate the variable focal length. The optically effective surfaces, which generate the variable focal length may include all optically effective surfaces of the beam expander, which are located upstream of the intermediate focus, relative to a light direction of the measurement beam toward the object.

The beam expander may include one or more controllably movable optical units. Each of the controllably movable optical units may be movable depending on control signals of a controller. A movable optical unit may be defined as a component, wherein all optically effective surfaces of the component are moved as a unit. In other words, the optically effective surfaces of the movable unit do not make any movements relative to each other.

The beam expander may be configured so that in order to adjust the different values of the beam waist diameter, the movable optical units move relative to each other. One or more of the movable optical units may be configured so that they perform a movement along and/or transverse relative to an optical axis of the beam expander. By way of example, the beam expander may include one or more Alvarez lenses. Alternatively or additionally, one or more of the movable optical units may be configured so that they are selectively insertable and removable from the measurement beam.

Alternatively or additionally, the beam expander may include one or more optical units, which have a controllably variable shape of a refractive or reflective surface and/or have a controllably variable refractive index. By way of example, the beam expander may include one or more liquid lenses.

According to a further embodiment, the beam expander is configured so that at different values of the variable focal length, a position of the intermediate focus along an axis of the measurement beam is identical or substantially identical. The position of the intermediate focus may be measured relative to a stationary reference point.

According to a further embodiment, the beam expander is configured so that at different values of the variable focal length, a position of an object-side focal plane of the beam expander is identical or substantially identical. The object-side focal plane may be generated by all optically effective surfaces of the beam expander. Alternatively, at the different values of the variable focal length, the beam expander may be an afocal system or substantially an afocal system.

According to a further embodiment, the beam expander comprises a first controllably movable optical unit, which has or includes a negative refractive power. The term "refractive power" may be understood as a spherical refractive power. In addition to the spherical refractive power, a cylindrical refractive power may or may not be present. The refractive power may be a local or a non-local refractive power. The refractive power may be generated by means of optically effective surfaces, which are rotationally symmetric spherical and/or rotationally symmetric aspherical. The optically effective surfaces, which generate the refractive power, may include one or more optically effective surfaces, which have a cylindrical optical power. The optically effective surfaces, which generate the refractive power, may be free from a cylindrical refractive power and/or free from aspherical surfaces. Furthermore, in the present disclosure, the terms first, second, third and fourth optical unit or movable optical unit are used in order to differentiate these units from each other. Therefore, for example, the feature "third optical unit" in an embodiment does not indicate that a first and a second optical element are included in the embodiment.

According to a further embodiment, the beam expander includes a second controllably movable optical unit, which has or comprises a positive spherical refractive power. The beam expander may be configured so that during a variation of the beam expansion, the first and the second movable optical units are moved relative to each other.

According to an embodiment, the first movable optical unit is arranged downstream or upstream of the second movable optical unit, relative to a light direction of the measurement beam toward the object. According to a further embodiment, the first and/or the second movable optical units are disposed upstream of the intermediate focus, relative to a light direction of the measurement beam toward the object.

According to a further embodiment, the beam expander includes a third optical unit. The third optical unit may be stationary or controllably movable. The third optical unit may include or have a negative or positive refractive power. The third optical unit may be located downstream of the first and/or the second movable optical units relative to a light direction of the measurement beam toward the object. According to a further embodiment, the third optical unit is disposed upstream of the intermediate focus, relative to a light direction of the measurement beam toward the object.

According to a further embodiment, the beam expander includes a fourth optical unit. The fourth optical unit may be stationary. The fourth optical unit may be disposed downstream of the intermediate focus, relative to a light direction of the measurement beam toward the object. The fourth stationary optical unit may have or include a positive refractive power. A focal length of the fourth stationary optical unit may be greater than 1.5 times, greater than 2 times or greater than 3 times a maximum value of the controllably variable focal length of the beam expander, which is used for focusing the measurement beam into the intermediate focus. This controllably variable focal length may be generated by all optically effective surfaces of the beam expander, which are disposed upstream of the intermediate focus, relative to the light path directed toward the object.

According to a further embodiment, the beam expander is configured so that the position of the object-side focal plane of the beam expander is controllably variable and/or so that the beam expander is controllably switchable between a focal and an afocal system.

The beam expander may be configured so that all optically effective surfaces of the beam expander, which are disposed upstream of the intermediate focus, relative to a light path directed toward the object, are moved along the optical axis as a unit for adjusting the position of the object-side focal plane. By virtue of the movement as a unit, these optically effective surfaces do not change their positions relative to each other.

Alternatively or additionally, for adjusting the position of the object-side focal plane, all optically effective surfaces of the beam expander, which are located downstream of the intermediate focus, relative to the light path directed toward the object, are controllably moved along the optical axis as a unit.

Alternatively or additionally, the OCT system may include optics, which are disposed upstream of the scanning system, relative to the light direction of the measurement beam toward the object. The optics may be configured as a collector optics for collecting light of the light entrance. The optics may be configured so that a section of the measurement beam, which emerges from the optics, is parallel or substantially parallel. The section of the measurement beam, which emerges from the optics may be a section of the measurement beam, which is incident on the scanning system.

According to a further embodiment, the optical system comprises a user interface, which comprises a plurality of control elements, wherein each of the control elements is selectively placeable into one of a plurality of different states. The optical system may further comprise a controller, which may be configured so that for each of the control elements, an operating parameter of the optical system is adjusted, depending on the selected state of the respective control element, so that via different control elements of the plurality of control elements, different operating parameters of the optical system are adjustable. For each of the control elements, the adjustment of the respective operating parameter may be performed according to a predefined dependency between the states and values of the operating parameters. The user interface may be switchable into a first and into a second operating mode. The controller may be configured so that in the first operating mode for each of the control elements, an operating parameter of the OCT system is adjusted. In the second operating mode, for each of the control elements, an operating parameter of the microscopy system may be adjusted.

The OCT image data may depend on the operating parameters of the OCT system. The image, which is generated in the image plane may depend on the operating parameters of the microscopy system.

Examples for control elements may be: electromechanical control elements, such as a food pedal, a control, as well as control elements of a graphical user interface. Examples for states of the control elements may be: a degree as to how much the food pedal is pressed, a turning position of the mechanical knob or the position of a slider, which is implemented through a graphical user interface.

According to a further embodiment, for a first one of the control elements, the operating parameter of the microscope system is a zoom magnification of the zoom system or depends on the zoom magnification. Alternatively or additionally, for the first control element, the operating parameter of the OCT system is a beam waist diameter of a beam waist of the measurement beam or depends on the beam waist diameter.

Alternatively or additionally, for a second control element of the plurality of control elements, the operating parameter of the microscope system may be an object plane distance of the object plane or may depend on the object plane distance. Alternatively or additionally, for the second control element, the operating parameter of the OCT system may be an axial beam waist position of the beam waist or may depend on the axial beam waist position.

The present disclosure relates to the following embodiments:

Item 1: An optical system for inspecting an eye, the optical system comprising: a microscopy system for generating an image of an object region in an image plane; an OCT system, which is configured to acquire OCT image data, wherein the OCT system generates a measurement beam, which is incident on the object region in a converging manner to form a measurement focus; and a user interface, which is selectively switchable into a coupled operating mode and into a decoupled operating mode; wherein in the coupled operating mode, an adjustment of a first operating parameter and an adjustment of a second parameter are limited to a predefined dependency between the first and the second operating parameters; wherein in the decoupled operating mode, the first and the second operating parameters are adjustable independently from the predefined dependency; wherein the acquired OCT image data depend on the first operating parameter and the image which is generated in the image plane depends on the second operating parameter.

Item 2: The optical system according to item 1, wherein the microscopy system comprises a zoom system for adjusting an imaging magnification of the generation of the image through a variation of a zoom magnification of the zoom system; wherein the first operating parameter is the zoom magnification or depends on the zoom magnification and the second operating parameter is a beam waist diameter of a beam waist of the measurement focus or depends on the beam waist diameter.

Item 3: The optical system according to item 1, wherein the object region is located in an object plane, which is optically conjugate to the image plane; wherein the first operating parameter is an object plane distance of the object plane or depends on an object plane distance and the second operating parameter is an axial beam waist position of a beam waist of the measurement focus or depends on the axial beam waist position.

Item 4: The optical system according to any one of the preceding items, wherein the object region is located in an object plane, which is optically conjugate to the image plane; wherein the user interface is configured so that a desired distance (d) between the object plane and a beam waist of the measurement focus is inputtable by a user input; wherein the user interface is configured for selection, whether at the desired distance: either a value of an object plane distance of the object plane is identical or substantially identical to a value of the object plane distance when the desired distance (d) is input; or whether a value of an axial beam waist position of the beam waist is identical or substantially identical to a value of the axial beam waist position, when the desired distance (d) is input.

Item 5: An optical system for inspecting an eye, the optical system comprising: a microscopy system for generating an image of an object region in an image plane, wherein the object region is located in an object plane, which is optically conjugate to the image plane; an OCT system, which is configured to generate a measurement beam, which is incident on the object region in a converging manner to generate a measurement focus, which comprises a beam waist at an axial beam waist position; and a user interface, which is configured so that a desired distance (d) between the object plane and the beam waist is inputtable by a user input; wherein the user interface is configured for selection, whether at the desired distance (d): either a value of an object plane distance of the object plane is identical or substantially identical to a value of the object plane distance, when the desired distance (d) is input; or whether a value of the axial beam waist position is identical or substantially identical to a value of the axial beam waist position, when the desired distance (d) is input.

Item 6: The optical system according to any one of the preceding items, wherein the microscopy system comprises a zoom system for varying an imaging magnification of the generation of the image through a variation of a zoom magnification of the zoom system; wherein the optical system comprises a controller for controlling a beam waist diameter of a beam waist of the measurement focus and for controlling the zoom magnification; wherein the controller is configured for a coupled control of the beam waist diameter and the zoom magnification according a predefined dependency between the beam waist diameter and the zoom magnification; wherein the controller is configured for selectively activating and deactivating the coupled control of the beam waist diameter and the zoom magnification.

Item 7: An optical system for inspecting an eye comprising: a microscopy system for generating an image of an object region in an image plane; wherein the microscopy system comprises a zoom system for varying an imaging magnification of the generation of the image through a variation of a zoom magnification of the zoom system; an OCT system, which is configured to generate a measurement beam, which is incident on the object region in a converging manner to form a measurement focus which comprises a beam waist; wherein the optical system comprises a controller for controlling a beam waist diameter of the beam waist and for controlling the zoom magnification; wherein the controller is configured for a coupled control of the beam waist diameter and the zoom magnification according to a predefined dependency between the beam waist diameter and the zoom magnification; wherein the controller is configured for selectively activating and deactivating the coupled control of the beam waist diameter and the zoom magnification.

Item 8: The optical system according to items 6 or 7, wherein the controller is further configured for a coupled control of the beam waist diameter and a length of an axial measurement range of the OCT system according to a predefined dependency between the beam waist diameter and the length of the axial measurement range.

Item 9: An optical system for inspecting an eye, the optical system comprising: an OCT system which is configured to generate a measurement beam, which is incident on an object region in a converging manner to form a measurement focus which comprises a beam waist; wherein the OCT system comprises a scanning system, an objective lens, and a beam expander, wherein the beam expander is configured for a controllable beam expansion of the measurement beam, wherein the scanning system, the objective lens and the beam expander are disposed in the measurement beam; wherein the beam expander is disposed along the measurement beam between the scanning system and the objective lens and generates an intermediate focus between the scanning system and the objective lens; wherein the OCT system is configured to generate different values of a beam waist diameter of the beam waist by means of controlling the controllable beam expansion; wherein at the different values of the beam waist diameter, an axial beam waist position of the beam waist is identical or substantially identical.

Item 10: The optical system according to item 9, wherein at each of the different values of the beam waist diameter, a position of an object-side focal plane of the beam expander is identical or substantially identical; or at each of the different values of the beam waist diameter, the beam expander is an afocal system or substantially an afocal system.

Item 11: The optical system according to item 9 or 10 further comprising a microscopy system, which is configured for generating an image of an object region in an image plane, wherein the object region is located in an object plane, which is optically conjugate to the image plane; wherein the microscope system is configured to generate an observation channel for generating the image, wherein the observation channel traverses the objective lens; wherein at the different values of the beam waist diameter, the beam waist is located outside of the object plane.

Item 12: The optical system according to any one of items 9 to 11, wherein a portion or all of the optically effective surfaces of the beam expander generate a controllably variable focal length for focusing the measurement beam to the intermediate focus.

Item 13: An optical system, comprising: an OCT system, which is configured to generate a measurement beam, which is incident on the object region in a converging manner to generate a measurement focus, which comprises a beam waist; wherein the OCT system comprises a scanning system, an objective lens and a beam expander, wherein the beam expander is configured for a controllable beam expansion of the measurement beam, wherein the scanning system, the objective lens and the beam expander are disposed in the measurement beam; wherein the beam expander is disposed along the measurement beam between the scanning system and the objective lens and generates an intermediate focus of the measurement beam between the scanning system and the objective lens; wherein a portion or all of the optically effective surfaces of the beam expander generate a controllably variable focal length for focusing the measurement beam to the intermediate focus.

Item 14: The optical system according item 12 or 13, wherein the beam expander is configured so that at different values of the variable focal length, a position of the intermediate focus along an axis of the measurement beam is identical or substantially identical.

Item 15: The optical system according to any one of items 12 to 14, wherein the beam expander is configured so that at different values of the variable focal length, a position of an object-side focal plane of the beam expander is identical or substantially identical; or at different values of the variable focal length, the beam expander (60) is an afocal system or substantially an afocal system.

Item 16: The optical system according to any one of items 9 to 15, wherein the beam expander comprises: a first controllably movable optical unit, which has or comprises a negative refractive power.

Item 17: An optical system for inspecting an eye, comprising: an OCT system, which is configured to generate a measurement beam, which is incident on an object region in a converging manner to generate a measurement focus, which comprises a beam waist; wherein the OCT system comprises a scanning system, an objective lens and a beam expander for a controllable beam expansion of the measurement beam, wherein the scanning system, the objective lens and the beam expander are disposed in the measurement beam; wherein the beam expander is disposed along the measurement beam between the scanning system and the objective lens and generates an intermediate focus of the measurement beam between the scanning system and the objective lens; wherein the beam expander comprises: a first controllably movable optical unit, which has or comprises a negative refractive power.

item 18: The optical system, according to item 16 or 17, wherein the beam expander further comprises: a second controllably movable optical unit, which has or comprises a positive refractive power; wherein the first and the second movable optical units are moved relative to each other when performing a variation of the beam expansion.

item 19: The optical system according to item 18, wherein the first and the second optical units are disposed upstream of the intermediate focus, relative to a light direction of the measurement beam toward the object.

Item 20: The optical system according to any one of the preceding items, further comprising a third optical unit, which has or comprises a negative refractive power and which is disposed downstream of a first and/or a second movable optical unit of the beam expander, relative to a light direction of the measurement beam toward the object.

Item 21: The optical system according to item 20, wherein the third optical unit is arranged upstream of the intermediate focus relative to the light direction of the measurement beam toward the object.

Item 22: The optical system according to any one of items 9 to 21, wherein the beam expander is controllable so that the beam expander is configurable between a focal system and an afocal system.

Item 23: The optical system according to any one of items 9 to 22, wherein the beam expander is configured so that a position of an object-side focal plane of the beam expander is controllably variable.

Item 24: The optical system according to any one of the preceding items, further comprising: a user interface, which comprises a plurality of control elements, wherein each of the control elements is selectively placeable into one of a plurality of different states; a controller, which is configured so that for each of the control elements, an operating parameter of the optical system is adjusted, depending on the selected state of the respective control element, so that via different control elements of the plurality of control elements, different operating parameters of the optical system are adjustable; wherein for each of the control elements, the adjustment of the respective operating parameter is performed according to a predefined dependency between the states and values of the operating parameters; wherein the user interface is switchable into a first and into a second operating mode; wherein the controller is configured so that in the first operating mode for each of the control elements, an operating parameter of the OCT system is adjusted and in the second operating mode, for each of the control elements, an operating parameter of the microscopy system is adjusted.

Item 25: An optical system for inspecting an eye, the optical system comprising: a microscopy system for generating an image of an object region in an image plane; an OCT system, which is configured to generate a measurement beam (9), which is incident on the object region in a converging manner to form a measurement focus; a user interface, which comprises a plurality of control elements, wherein each of the control elements is selectively placeable into one of a plurality of different states; a controller, which is configured so that for each of the control elements an operating parameter of the optical system is adjusted, depending on the selected state of the respective control element, so that via different control elements of the plurality of control elements, different operating parameters of the optical system are adjustable; wherein for each of the control elements, the adjustment of the respective operating parameter is performed according to a predefined dependency between the states and values of the operating parameters; wherein the user interface is switchable into a first and into a second operating mode; wherein the controller is configured so that in the first operating mode for each of the control elements, an operating parameter of the OCT system is adjusted and in the second operating mode, for each of the control elements, an operating parameter of the microscopy system is adjusted.

Item 26: The optical system according to item 24 or 25, further comprising a zoom system for varying an imaging magnification of the generation of the image through a variation of a zoom magnification of the zoom system, wherein for a first one of the control elements, the operating parameter of the microscopy system is the zoom magnification of the zoom system or depends on the zoom magnification and the operating parameter of the OCT system is a beam waist diameter of a beam waist of the measurement beam or depends on the beam waist diameter.

Item 27: The optical system according to one of items 24 to 26, wherein an object plane, which is optically conjugate to an image plane is located in the object region; wherein for a second control element of the plurality of control elements, the operating parameter of the microscope system depends on an object plane distance of the object plane or depends on the object plane distance, and the operating parameter of the OCT system is an axial beam waist position of a beam waist of the measurement focus or depends on the axial beam waist position.

BRIEF DESCRIPTION OF THE DRAWINGS

The preceding as well as further advantageous features of the disclosure are more clearly outlined by the following detailed description of exemplary embodiments by referring to the accompanying figures. It is underlined that not all possible embodiments of the present disclosure necessarily produce some or all of the mentioned advantages.

FIG. 5 is a schematic illustration of the beam expander and the objective lens of the optical system, which is shown in FIGS. 1 and 4;

FIGS. 6A-C are schematic illustrations of different configurations of the beam expander of the optical system, which is shown in FIGS. 1 and 4 for adjusting the beam waist diameter of the OCT measurement beam; and FIG. 7 is a detailed illustration of the beam expander, which is shown in FIGS. 5 and 6.

DETAILED DESCRIPTION OF EXEMPLARY EMBODIMENTS

Figure 1:
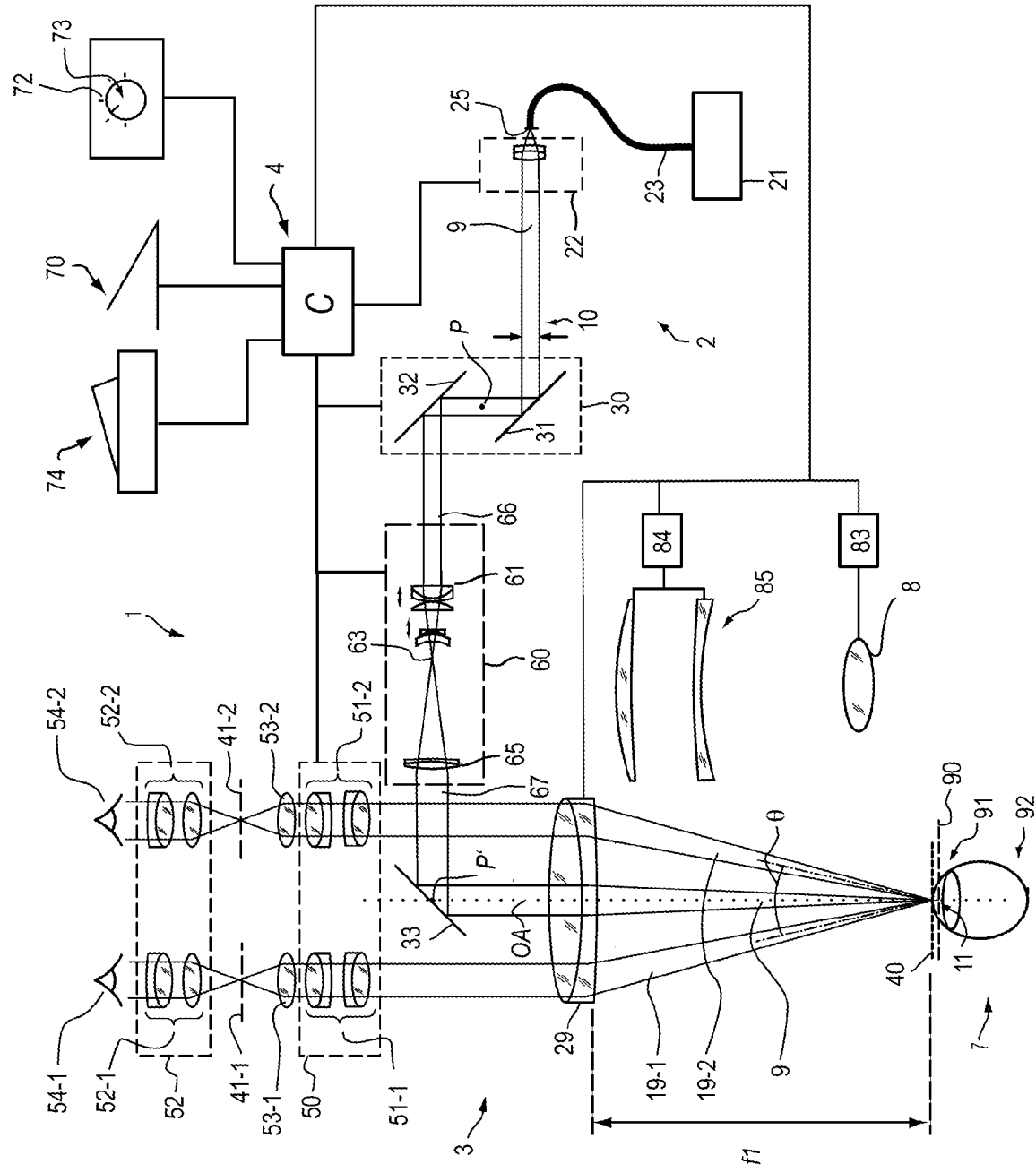
FIG. 1 is a schematic illustration of an optical system according to an exemplary embodiment, wherein the optical system is configured for inspecting an anterior section of the eye.

In the exemplary embodiments described below, components that are alike in function and structure are designated as far as possible by alike reference numerals. Therefore, to understand the features of the individual components of a specific embodiment, the descriptions of other embodiments and of the summary of the disclosure should be referred to.

FIG. 1 is a schematic illustration of an optical system 1 according to an exemplary embodiment.

FIG. 1 shows the optical system in a first operating mode, in which an object region in the anterior section 91 of the eye 7, such as a portion of the cornea, is imageable. As will be further described below with reference to FIG. 4, the optical system 1 can be operated in a second operating mode, in which an object region in the posterior section 92 of the eye 7 is imageable, such as a portion of the retina.

The optical system 1 includes an OCT system 2 and a microscope system 3. The microscope system 3 is configured as a stereoscopic microscope. The microscope system 3 is configured to generate two observation channels 19-1, 19-2, the axes of which intersect in the object plane 40 at a stereo angle θ. Each of the stereoscopic observation channels 19-1, 19-2 generates a stereoscopic partial image in an image plane 41-1, 41-2 of the respective observation channel 19-1, 19-2 of the object region, in which the object plane 40 is arranged.

In the first operating mode, which is shown in FIG. 1, a ray bundle of the first or the second observation channel 19-1, 19-2, which emanates from a point in the object plane 40, is converted by an objective lens 29 of the microscope system 3 into a bundle of rays, which is parallel or substantially parallel. The microscope system 3 includes a zoom system 50, which is disposed in the beam path of the observation channels 19-1, 19-2 downstream of the objective lens 29. The zoom system 50 includes two zoom components 50-1, 50-2, each of which being traversed by rays of one of the observation channels 19-1, 19-2. Each of the two zoom components 50-1, 50-2 may be configured as an afocal optical system. Each of the zoom components 50-1, 50-2 comprises movable optical components, which are drivingly mechanically connected to one or more actuators (not shown in FIG. 1). The actuators are in signal communication with a controller 4. Through signals of the controller 4, transmitted to the actuators, a zoom magnification of the zoom system 50 is adjustable. A zoom magnification may be, for example, a magnification factor, such as "2 times" or "3 times", by which the zoom system 50 magnifies the generation of the images in the image planes 41-1, 41-2. The magnification factor of the image generation in the image planes 41-1, 41-2 depends thereby on the zoom magnification.

For each of the observation channels 19-1, 19-2, the microscope system 3 includes respective focusing optics 53-1, 53-2. For each of the observation channels 19-1, 19-2, the focusing optics 53-1, 53-2 are configured to focus bundles of rays of the observation channels 19-1, 19-2, which emanate from a point in the object plane 40 at a point in the image plane 41-1, 41-2. The image planes 41-1, 41-2 are thereby optically conjugate to the object plane 40.

For each of the observation channels 19-1, 19-2, the microscope system 3 further comprises an ocular 52-1, 52-2. Through the oculars 52-1, 52-2, the partial images, generated in the image planes 41-1, 41-2, are visible to the eyes 54-1, 54-2 of an observer. Additionally or alternatively, it is conceivable that the optical system 1 comprises one or more image sensors (not shown in FIG. 1). The image sensor may be disposed in one of the image planes 41-1, 41-2 or in a plane, which is optically conjugate to one of the image planes 41-1, 41-2. The image sensor may be configured to acquire one of the generated partial images.

The OCT system 2 includes an interferometer which generates a measurement arm and a reference arm. The interferometer causes light, which has passed along the measurement arm to interfere with light, which has passed through the reference arm.

The OCT system 2 generates a measurement beam 9, which is guided along the measurement arm to the eye 7 in a light direction oriented toward the object. Scattered light of the measurement beam 9 is guided back along the measurement arm in a reversed direction relative to the light direction oriented toward the object. The light, which is guided back is caused to interfere with light, which has passed through the reference arm.

The measurement beam optics of the OCT system forms the measurement beam 9 so that the measurement beam 9 is incident on the object 7 in a converging manner to form a measurement focus 11. In an OCT unit 21, light of the measurement beam 9 is generated and guided via a light guide 23 to the measurement beam optics. Through a light exit surface 25, which is located at an end of the light guide 23, light of the measurement beam 9 is emitted into the measurement beam optics. The light exit surface 25 thereby forms a light entrance into the measurement beam optics. The measurement beam optics are imaging optics, which image the light exit surface 25 into the measurement focus 11.

The measurement beam optics include collector optics 22, a scanning system 30, a beam expander 60, a deflecting element 33 and an objective lens 29. The objective lens 29 is therefore part of the microscopy system 3 as well as of the measurement beam optics of the OCT system. The collector optics 22 are configured so that a section 10 of the measurement beam, which emerges from the collector optics is parallel or substantially parallel.

The scanning system 30 is configured to two-dimensionally laterally scan the measurement focus 11. Thereby, the measurement focus 11 is moved within a scanning plane 90. The scanning system 30 includes two scanning mirrors 31, 32, each of which being pivotally mounted.

Figure 2:
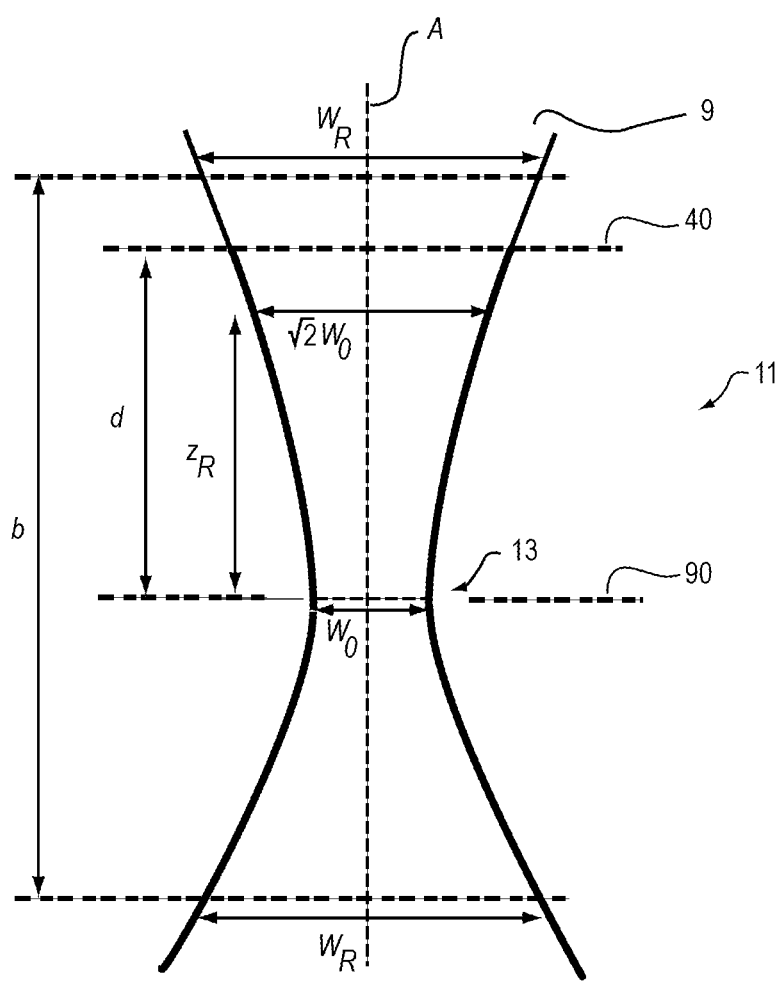
FIG. 2 is a schematic illustration of the measurement focus of the measurement beam of the OCT system of the optical system, which is shown in FIG. 1.

The measurement focus 11 and the measurement beam 9 are shown in detail in FIG. 2. The axial position, relative to the axis A of the measurement beam, at which the measurement focus 11 has a narrowest constriction, is defined as the beam waist 13. At the beam waist 13, the measurement beam, as beam waist diameter $W_0$. Through the laterally scanning of the measurement focus 11, the beam waist 30 is moved within the scanning plane 90. Through signals of the controller, the OCT measurement optics is configured so that a distance d between the beam waist 13 and the object plane 40 is adjustable. The distance d thereby denotes also the distance between the scanning plane 90 and the object plane 40.

The optical system 1 is configured for selective coupled and decoupled control of the beam waist diameter $W_0$ and the zoom magnification of the zoom system 50 (shown in FIG. 1). The coupled control is performed according to a predefined dependency between the beam waist diameter $W_0$ and the zoom magnification. By way of example, the predefined dependency is linear or substantially linear. The predefined dependency between the beam waist diameter $W_0$ and the zoom magnification may be for example so, that the beam waist diameter $W_0$ decreases with increasing zoom magnification.

It has been shown that such a coupled control is advantageous for the surgeon, since the surgeon can comparatively quickly adapt the zoom magnification and the beam waist diameter $W_0$ simultaneously, allowing him during surgical procedures to image different portions of the eye in a time efficient manner with the OCT system and the microscope system at different magnification levels. In particular, the surgeon is enabled to quickly switch the microscope system and the OCT system between acquisition of detail view images and acquisition of overview images.

Through input via a control element, the user may select between the coupled and the decoupled control of the beam waist diameter $W_0$ and the zoom magnification. During the decoupled control, the control of the beam waist diameter and the zoom magnification is independent from the pre-defined dependency. Thereby, values for the beam waist diameter and the zoom magnification are adjustable so that they do not satisfy the pre-defined dependency.

It has been shown that this is very advantageous for the surgeon. Initially, the surgeon may, by using the coupled control, select a starting point for further inspections by means of overview images and detail view images. By way of example, during a glaucoma surgery in the interior section of the eye, the surgeon may adjust the zoom magnification and the beam waist diameter $W_0$ in a coupled manner so that the Schlemm's canal can be imaged at a high resolution by using the microscopy system and the OCT system. Likewise, by using the coupled control, the surgeon may also image a selected location of an epiretinal membrane by using the microscopy system and the OCT system.

Thereafter, by using the user interface, the surgeon may switch the optical system to the decoupled control. In the decoupled control, the surgeon may, for example, further reduce the beam waist diameter of the OCT system in a decoupled manner from the zoom magnification of the microscopy system. The reduced beam waist diameter allows the surgeon, by using the OCT system at a high lateral resolution, to image individual selected subsections of the microscope's visual field, which are identifiable in the microscope image. This allows efficient and thorough inspection of tissue portion in the eye.

Figure 3:
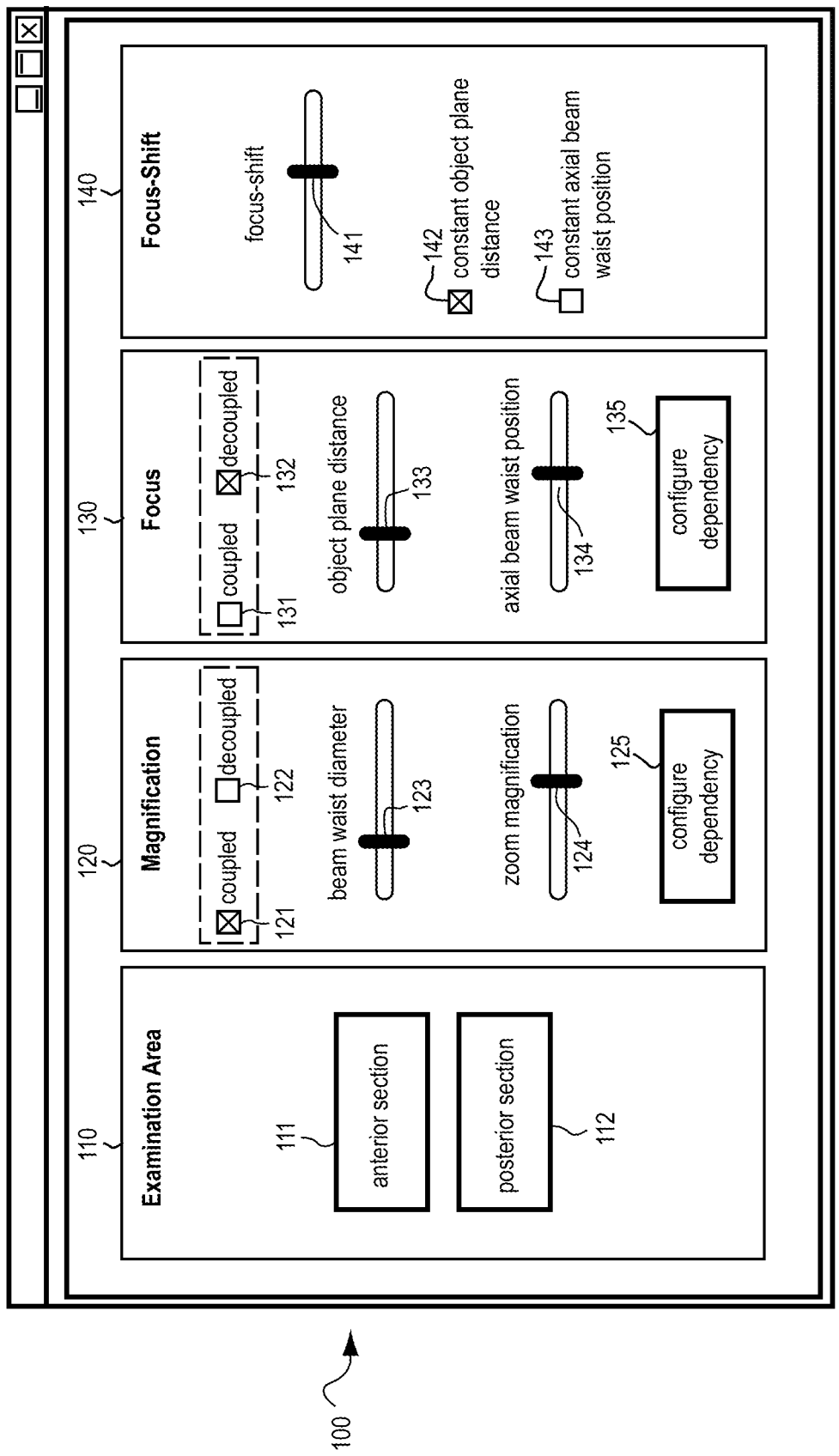
FIG. 3 is a schematic illustration of a window of a graphical user interface of the optical system which is shown in FIG. 1.

FIG. 3 shows a window 100 of a graphical user interface of the optical system 1. The graphical user interface is configured so that the user can vary a plurality of operating parameters of the microscope system and the OCT system. The graphical user interface can be displayed on a display device of a computer (not shown in FIG. 1) of the optical system.

The graphical user interface includes an operation area 120, in which the control elements are provided with which the user can adjust the beam waist diameter and the zoom magnification.

The operation area 120 includes checkboxes 121, 122 as control elements. By actuating or deactivating the checkboxes 121, 122, and the user can select, whether the operation of the graphical user interface for adjusting the beam waist diameter and the zoom magnification is performed in a coupled or decoupled manner. Thereby, the user interface is configured for selective coupled and decoupled user operation for adjusting the beam waist diameter and the zoom magnification.

If the user, by activating the checkbox 122, selects the coupled user operation of the beam waist diameter and the zoom magnification, the coupled control of the zoom magnification and the beam waist diameter is activated.

The operation area 120 includes a slide control 123 as operation element for adjusting the beam waist diameter and a slide control 124 as operation element for adjusting the zoom magnification. If the user, by activating the agape box 121, has activated the coupled control of the beam waist diameter and the zoom magnification, the adjusted positions of the slide controls 123 and 124 are coupled according to a pre-defined dependency. Theses slide controls 123 and 124 are then not adjustable independently from each other. Thereby, the user interface is in an operating mode, in which the coupled user operation is performed for a coupled adjustment of the zoom magnification and the beam waist diameter.

On the other hand, if the user, by activating the checkbox 122, has activated the decoupled control of the beam waist diameter and the zoom magnification, the adjusted positions of the slide controls 123 and 124 are decoupled from each other. These slide controls 123 and 124 are then adjustable so that the adjustable values do not satisfy the predefined dependency. Thereby, the user interface is in an operating mode, in which a decoupled user operation is performed for a decoupled adjustment of the zoom magnification and the beam waist diameter.

The operation area 120 further comprises a button 125. By operating the button 125, a further window is opened via which the user can configure the predefined dependency between the beam waist diameter and the zoom magnification. By way of example, via this further window, the user may vary a slope of a linear dependency between the beam waist diameter and the zoom magnification.

The graphical user interface further comprises a control area 130. The control area 130 includes a slide control 133 as a control element for adjusting an object plane distance of the object plane 4 (shown in FIG. 1). The object plane distance may be, for example, defined as a distance of the object plane 40 from the objective lens 29. Further, the control area 130 comprises a slide control 134 as a control element for adjusting the axial beam waist position of the beam waist 13 (shown in FIG. 2). The axial beam waist position is measured relative to the axis of the measurement beam 9. The control area 130 comprises a checkbox 131 for activating a coupled user operation for adjusting the object plane distance and the axial beam waist position. If the user has activated checkbox 131, signals transmitted to the controller for activating a coupled user control of the object plane distance and the axial beam waist position. The user interface is then in an operation mode, in which the adjusted positions of the slide controls 133 and 134 are coupled with each other. Then, the slide controls 133 and 134 are only adjustable so that the adjusted values correspond to the predefined dependency.

The coupled user control of the object plane distance and the axial beam waist position is performed according to a predefined dependency between these parameters. By way of example, the predefined dependency is configured so that the axial beam waist position and the object plane distance are disposed at a constant distance from each other, at least within a predefined range of the object plane distance. By way of example, for keeping the distance constant, the entire optical system may be displaced in a direction along the optical axis of the objective lens.

The control area 130 further includes a button 135. By operating the button 135, a further window is opened through which the user can configure the predefined dependency between the object plane distance and the axial beam waist position.

It has been shown that this coupled user operation is very advantageous for the surgeon during surgical procedures. Notably, this allows the surgeon to position the object plane of the microscope system at the anterior surface of the cornea of the eye and at the same time to position the beam waist of the OCT measurement beam at the posterior surface of the cornea. By shifting the object plane, different areas of the cornea are imaged at sharp focus by the imaging process of the microscopy system 3. As a result of the constant distance between the object plane and the axial beam waist position achieved by means of the coupled control, it is possible for a surgeon to comparatively quickly image by means of OCT the posterior surface of the cornea behind the portions of the anterior surface of the cornea which are imaged at a sharp focus.

On the other hand, if the user, by activating the checkbox 132, has activated the decoupled control of the object plane distance and the axial beam waist position, adjustments of the slide controls 133 and 134 are decoupled from each other. Then, the slide controls 133 and 134 are adjustable so that the adjusted values do not satisfy the predefined dependency. Thereby, the user interface is in an operation mode, in which a decoupled user operation is performed for adjusting the object plane distance and the axial beam waist position.

The graphical user interface further comprises a control area 140. The control area 140 includes a slide control 141 as a control element for inputting a desired distance (d) (shown in FIG. 2) between the object plane 40 and the beam waist 13. The control area 140 further includes checkboxes 132 and 133. Through the checkboxes 132 and 133, the user can select whether at the desired distance, either the value of the object plane distance or the value of the axial beam waist position is substantially identical to the value of the respective parameter when the desired distance is input through the slide control 141. The variation of the distance (d) in thereby performed so that at the varied distance, selectively, either the axial beam waist position or the object plane distance has its former value.

It has been shown that this allows the surgeon to efficiently use the optical system during surgical operations. By way of example, the surgeon, by using the coupled user operation of the object plane distance and the axial beam waist position, can position the object plane and the beam waist at a portion of the anterior surface of the cornea. Then, the surgeon can decouple the user operation by activating checkbox 132. By activating checkbox 142 and operating the slide control 141, the surgeon can keep the object plane position at the anterior portion of the cornea and position the beam waist at deeper layers of the cornea or at the posterior surface of the cornea. Depending on the microscope image of the anterior portion of the cornea, the surgeon may select portions, in which he intends to acquire OCT images of the deeper layers or of the posterior surface of the cornea. This allows the surgeon to efficiently use the optical system during surgical operations.

FIG. 2 schematically shows the beam path in the region of the measurement focus 11, in which the measurement beam can be described in good approximation as a Gauss beam. For a Gauss beam, the Rayleigh length is a measure for the increase of the lateral extent of the beam with increasing distance from the beam waist 13. The Rayleigh length may be defined as the distance $z_R$ along the axis A of the measurement beam 9, at which the cross-sectional area of the measurement beam has doubled, compared to the beam waist 13. According to this definition, at a distance $z_R$ from the beam waist 13, which corresponds to the Rayleigh length, the diameter of the measurement beam is $\sqrt{2}$ times the beam waist diameter $W_0$ at the location of the beam waist 13.

For Gauss beams, the following relationship between the Rayleigh length $z_R$ and the beam waist diameter $W_0$ holds:

$$z_R = \frac{W_0^2 \pi}{4\lambda}$$

wherein $\lambda$ is the wavelength of the measurement beam 9. Thus, the maximum beam diameter within the axial measurement range depends on the beam waist diameter $W_0$.

The optical system is configured for a coupled control of the beam waist diameter $W_0$ and the length b of the axial measurement range of the OCT system. The coupled control is performed according to a predefined dependency between the beam waist diameter $W_0$ and the length b of the axial measurement range.

Given a predefined minimum value for the lateral resolution, it is thereby possible to adjust the axial measurement range for different values of the beam waist diameter $W_0$. The predefined dependency may be defined so that over the entire axial measurement range, the lateral resolution does not pass below the predefined minimum value for the lateral resolution. The length b of the axial measurement range may be determined as large as possible taking in to consideration the predefined minimum value for the lateral resolution. Then, the diameter $W_R$ of the measurement beam at the limits of the axial measurement range represents the predefined minimum value of the lateral resolution. If the limits of the axial measurement ranges are exceeded, the lateral resolution is lower than the pre-defined minimum value.

By virtue of the coupled control of the beam waist diameter $W_0$ and the length b of the axial measurement range, its is avoided that during a surgical operation, OCT data are acquired, which, due to low resolution, are useless or which may lead to misdiagnoses. This increases the reliability of intraoperative image evaluation processes and increases image acquisition speed.

As is illustrated in FIG. 1, the beam expander 60 is disposed between the scanning system 30 in the objective lens 29. The beam expander 60 is configured to expand a diameter of a section of the measurement beam, which is incident on a source side of the beam expander 60 so that a section 67 of the measurement beam, which emerges from the beam expander 60 on an object side of the beam expander 60, has a greater diameter. The diameter of the emerging section 67 of the measurement beam may be, for example, at least 1.5 times or 2 times the diameter of the incident section 66. By virtue of the beam expansion, it can be achieved that the measurement beam 9 is incident on the measurement focus 11 in a converging manner with a high numerical aperture. Thereby, it is possible to obtain a comparatively low diameter $W_0$ (shown in FIG. 2) of the beam waist 13.

The beam expander 60 is configured so that an intermediate focus 63 is generated between the scanning system 30 and the objective lens 29. The beam expander is further configured so that a point P on the axis of the measurement beam 9 between the two scanning mirrors 31 and 32 is imaged onto a point P', which is located on the axis of the measurement beam 9, and which is located substantially on a refractive surface of the deflecting element 33. Thereby, an amount of a movement of the measurement beam on the deflecting element 33, which is generated by a scanning movement of the scanning mirrors 31, 32 can be kept small.

The beam expander 60 is configured for a controllable beam expansion. For controlling the beam expansion, the beam expander 60 is in signal communication with the controller 4. Through different values of the beam expansion, different values of the numerical aperture of the measurement beam 9 at the location of the measurement focus may be obtained. By the different values of the numerical aperture, different for the beam waist diameter may be obtained.

The beam expander 60 is configured so that at the different values of the beam expansion, the position of the object side focal plane of the beam expander is identical, or that for the different values of the beam expansion, the beam expander is an afocal system. Thereby, the axial beam waist position of the measurement beam can be kept constant for different values of the beam waist diameter. This allows adaptation of the lateral resolution of the OCT data without the need to readjust the axial position of the beam waist or the object plane distance. Since the different values of the beam waist diameter are generated by different values of the beam expansion, the object plane distance may be kept constant when the lateral resolution of the OCT data is adjusted, since, for adjusting the beam waist diameter, no adjustment of the focal length of the objective lens 29 is necessary.

The beam expander 60 is configurable by signals of the controller 4 so that at each of the different values of the beam waist diameter, the beam waist is located outside of the object plane. By way of example, this allows the surgeon to adjust the lateral resolution in examinations, in which the axial measurement range of the OCT system is outside of the object plane. In the illustrated exemplary embodiment, this is achieved by virtue of an identical position of the object side focal plane of the beam expander 60 for each of the different values of the beam expansion.

Alternatively or additionally, by using signals of the controller 4, the beam expander 60 is configurable so that the beam expanders 60 is an afocal system for different values of the beam expansion. Then, the beam waist of the measurement beam is located in the object plane 40, since the measurement beam is incident on the objective lens 29 as a parallel beam. This allows the surgeon to vary the beam waist diameter without displacing the beam waist from the object plane 40.

The graphical user interface includes a control area 110 (shown in FIG. 3), which includes buttons 111 and 112. By operating one of the buttons 111 or 112, the user can switch the optical system to the first or the second operating mode for selecting between an inspection of the interior section of the eye and an inspection of the posterior section of the eye.

Figure 4:
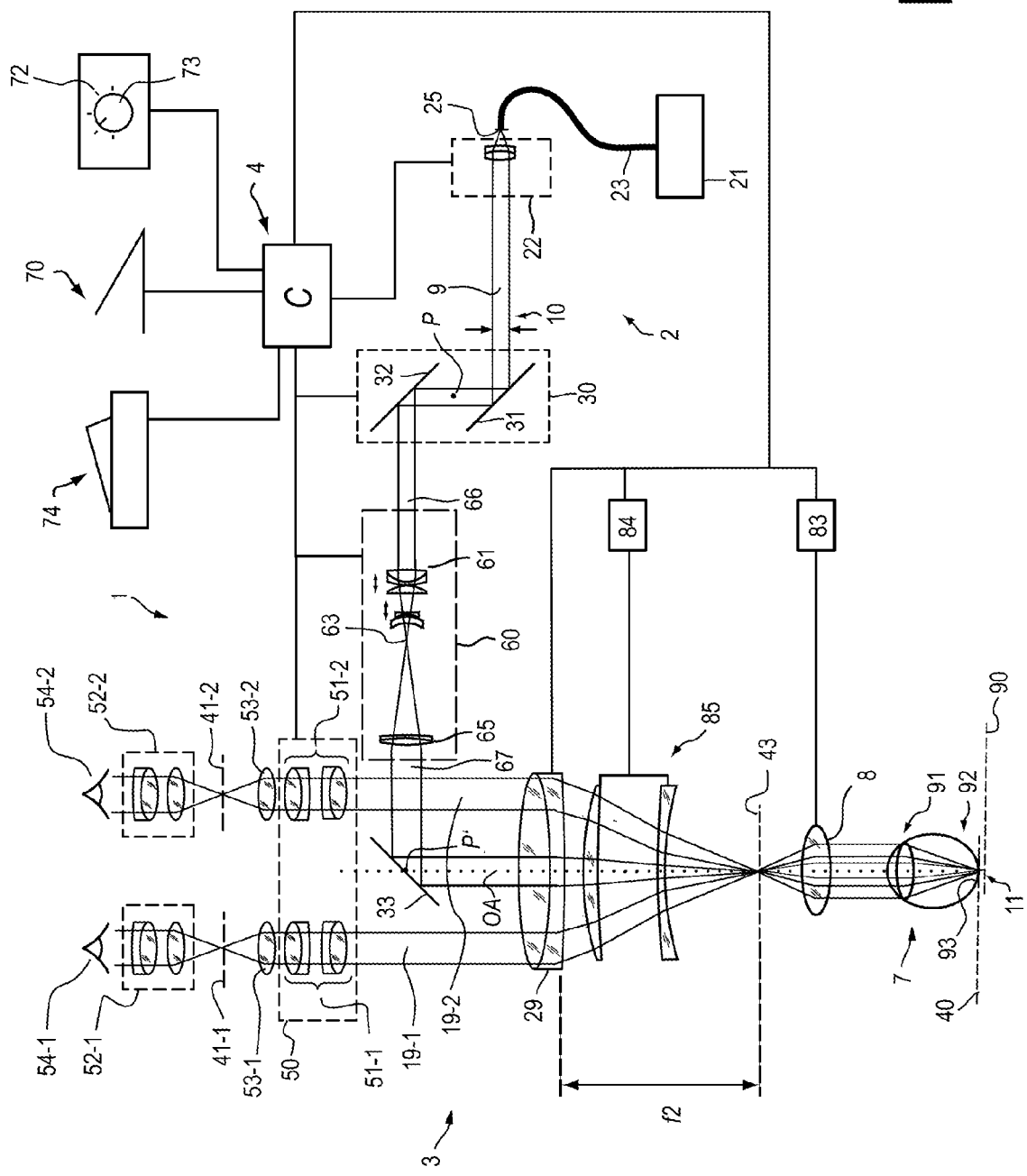
FIG. 4 shows the optical system of FIG. 1 in an operation mode for imaging an object region of a posterior section of the eye.

FIG. 4 shows the optical system in the second operating mode, which is configured for inspection of the posterior section 92. When switching into the second operating mode, a reducing lens system 85 and an ancillary ophthalmoscopy module 8 is inserted into the beam path of the observation channels 19-1 and 19-2 as well as into the beam path of the measuring beam 9 between the objective lens 29 and the eye 7. To this effect, the reducing lens system 85 is mechanically driven by an actuator 84 and the ancillary ophthalmoscopy module 8 is mechanically driven by an actuator 83.

In the second operating mode, the focal plane 43 of an optical system consisting of the objective lens 29 and the reducing lens system 85 is located between the reducing lens system 85 and the ancillary ophthalmoscopy module 8. By varying the focal length of the objective lens 29, the focal length $f_2$ is adjusted so that the object plane 40 of the microscope system 3 and the beam waist of the measurement beam 9 are located at desired positions in the posterior section 92 of the eye 7, such as on the retina 93. In order this to be achieved for an emmetropic eye which is accommodated to infinity, the focal plane 43 needs to be located in the focal plane of the ancillary ophthalmoscopy module 8.

FIG. 5 illustrates the configuration of the beam expander 60. The beam expander 60 includes a first optical component 64 and a second optical component 65. The first optical component 64 focuses the incident section 66 of the measurement beam 9 into an intermediate focus 63. Relative to the light direction of the measurement beam 9 toward the object, the intermediate focus 63 is located downstream of the first optical component 64 and upstream of the second optical component 65.

The second optical component 65 is configured to be stationary and comprises a positive refractive power. The first optical component 64 includes movable optical units and stationary optical units. The movable optical units are mechanically drivingly connected to actuators (not shown in FIG. 5), wherein the actuators are in signal communication with the controller. Depending on signals of the controller, each of the movable optical components is movable along the optical axis of the beam expander 60. The beam expander 60 is configured so that by the movement of the movable optical components, the focal length of the first optical component 64 is adaptable so that for different values of the focal length, the position of the intermediate focus on the axis of the measurement beam is identical. Thereby, different values of the beam waist diameter may be obtained, wherein the axial beam waist position is identical. This is explained in detail further below with reference to FIGS. 6A to 6C.

The beam expander 60 is configured so that a position of an object side focal plane of the beam expander is controllably variable. In other words, by using signals of the controller, the position of the object side focal plane of the beam expander is variable. The focal plane is generated by all optically effective surfaces of the beam expander 60. Thereby, the beam expander 60 is configurable between a focal system and an afocal system, depending on signals of the controller. The OCT system is configured so that the axial beam waist position is adjustable by means of an adjustment of the position of the object side focal plane. The beam expander may be configured so that the first optical component 64 is controllably movable as a unit along the optical axis of the beam expander 60, wherein all optically effective surfaces of the first optical component 64 are moved as a unit. The optically effective surfaces thereby do not perform any movement relative to one other. Thereby, it is possible to vary the axial beam waist position.

Additionally or alternatively, it is conceivable that the second optical component 65 is controllably movable along the optical axis. Since the second optical component 65 has a greater focal length compared to the first optical component 64, for obtaining the same variation in refractive power, the second optical component is needs to be displaced over a longer displacement path, compared to the first optical component 64. Moving the second optical component 65 thereby allows an adjustment of the axial beam waist position in reproducible manner over a smaller range at a comparatively high precision. On the other hand, moving the first optical component 64 allows adjustment of the beam waist position in a reproducible manner over a comparatively large range.

The OCT system is further configured for a coupled control of the axial beam waist position and the axial position of the axial measurement range of the OCT system. In particular, the axial measurement range may be displaced by the same amount as the axial beam waist position. Thereby, it is possible to keep the beam waist substantially in the middle of the axial measurement range. The position of the axial measurement range may be for example adapted by varying the optical path length of the reference beam, for example, by varying a position of the reference mirror.

FIGS. 6A to 6C show different configurations of the beam expander 60, which generate different beam expansions of the measurement beam 9. By using signals of the controller, the beam expander 60 was configured as an afocal system. In this configuration, the beam expander forms a Kepler telescope and the beam waist of the measurement beam is located in the object plane. By using signals of the controller, the beam expander 60 is also configurable so that the beam expander 60 deviates from the afocal configuration. Thereby, the beam waist 13 (shown in FIG. 2) is positionable so that it is located outside of the object plane 40.

The configuration of FIG. 6A expands the diameter of the incident section 66 of the measurement beam 9 by a factor of 8.94. In other words, the diameter of the emerging section of the measurement beam 9 on the object side of the beam expander 60 is 8.94 times the diameter of the incident section 66 of the measurement beam 9 on the source side of the beam expander 60. The configuration of FIG. 6B expands the diameter of the incident section 66 of the measuring beam by a factor of 6.35. The configuration of FIG. 6C expands the diameter of the incident section 66 of the measurement beam by a factor of 4.49. Accordingly, with the configuration of FIG. 6A, a mall beam waist diameter can be obtained, with the configuration of FIG. 6B a medium beam waist diameter and with the configuration of FIG. 6C a large beam waist diameter can be obtained.

The first optical component 64 comprises a first movable optical unit 81, which comprises a negative refractive power. Furthermore, the first optical component 64 comprises a second movable optical unit 80, which comprises a positive refractive power. Furthermore, the first optical component 64 comprises a third stationary optical unit 82, which comprises a negative refractive power. The first and the second movable optical components 80, 81 are movable for adjusting the beam expansion along the optical axis.

By moving the movable optical components 80, 81 the focal length of the first optical component 64, through which the intermediate focus 63 is generated, is variable. The first optical component 64 is configured so that the position of the intermediate focus 63 along the measurement beam 9 is identical for different values of the variable focal length. The position of the intermediate focus 63 may be measured when the scanning mirrors 31, 32, are undeflected, when the axis of the measurement beam 9 extends along the optical axis of the beam expander 60.

Thereby, it is possible that for all adjustments of the beam expansion, the beam expander is an afocal system (as shown in FIGS. 6A to 6C). Thereby, it is possible to obtain different values for the beam waist diameter, wherein for each of the values the beam waist is located in the object plane.

In a similar way, the constant position of the intermediate focus 63 in configurations of the beam expander, in which the beam expander deviates from an afocal configuration (not shown) makes it possible that the position of the object side focal plane of the beam expander is identical for different values of the variable focal length. Thereby, it is possible to obtain different values for the beam waist diameter, wherein for each of the values, the distance of the beam waist from the object plane of the microscope system is identical.

FIG. 7 is a detailed illustration of the beam expander 60, wherein the first component 64 is depicted in the upper portion of FIG. 7 and the second component 65 is depicted in the lower portion of FIG. 7. The deflecting elements 31, 32 of the scanning system also illustrated only in a schematic manner. Optical data of the beam expander are given in Table 1. The values listed in the column entitled as "zoom 1" relate to the configuration, which is shown in FIG. 6A. The values listed in the column entitled as "zoom 2" relate to the configuration, which is shown in FIG. 6B. The values listed in the column entitled as "zoom 3" relate to the configuration, which is shown in FIG. 6C.

TABLE 1

| Surface | Radius [mm] | Thickness [mm] | | | Diameter [mm] | Glass-type | Refractive index at 1060 nm |
| --- | --- | --- | --- | --- | --- | --- | --- |
| | | Zoom 1 | Zoom 2 | Zoom 3 | | | |
| object plane | ∞ | 18.00 | 15.18 | 9.35 | | air | |
| S1 | 49.70 | 3.00 | 3.00 | 3.00 | 10.00 | PSK52 | 1.5919 |
| S2 | −6.50 | 1.00 | 1.00 | 1.00 | 10.00 | SF57 | 1.8119 |
| S3 | −12.70 | 0.10 | 0.10 | 0.10 | 10.00 | air | |
| S4 | 8.40 | 2.00 | 2.00 | 2.00 | 10.00 | PSK52 | 1.5919 |
| S5 | ∞ | 5.11 | 2.95 | 1.4 | 10.00 | air | |
| S6 | −49.70 | 0.50 | 0.50 | 0.50 | 6.00 | PSK52 | 1.5919 |
| S7 | 6.50 | 0.50 | 5.57 | 12.8 | 5.60 | air | |
| S8 | 8.40 | 1.70 | 1.70 | 1.70 | 8.00 | PSK52 | 1.5919 |
| S9 | 6.50 | 96.75 | 96.75 | 96.75 | 7.40 | air | |
| S10 | 176.40 | 1.00 | 1.00 | 1.00 | 20.00 | SF57 | 1.8119 |
| S11 | 52.20 | 2.50 | 2.50 | 2.50 | 20.00 | PSK52 | 1.5919 |
| S12 | −59.85 | 3.00 | 3.00 | 3.00 | 20.00 | air | |
| image plane | | | | | | | |

The first optical unit 81 is configured as a lens having a negative refractive power and includes optically effective surfaces S6 and S7. The second movable optical unit 80 includes a cemented element having a positive overall refractive power. The cemented element includes optically effective surfaces S1, S2 and S3. Furthermore, the second optical unit 80 includes a lens having a positive refractive power and which includes optically effective surfaces S4 and S5. The lens is arranged downstream of the cemented element, relative to a light path of the measurement beam 9 directed toward the object. The third optical unit 82 is configured as a lens having a negative refractive power and which includes optically effective surfaces S8 and S9.

As is shown in FIGS. 1 and 4, the optical system 1 includes a foot pedal 70 as a control element, as well as a knob 73 as a control element. Each of these control elements can be placed into plurality of states. By way of example, the foot pedal 70 is configured so that the foot pedal 70 can be brought into different pedal positions by different values of a pressing force applied by the user's foot. Each of the pedal positions corresponds to a state. Depending on the pedal position, signals are transmitted to the controller 4. The knob 73 is configured so that different turning positions of the knob 73 relative to a scale 72 cause different signals to be transmitted to the controller 4. Thereby, the different turning positions represent a plurality of states.

For each of these control elements, the controller 4 is configured so that, depending on the selected state of the control element, an operating parameter of the optical system 1 is adjusted, wherein by means of the different operating elements (i. e. by using the foot pedal 70 and the knob 73), different operating parameters of the optical system 1 are adjusted. Each of the operating parameters is adjusted by the controller 4 according to a predefined dependency between the states of the respective control element and values of the operating parameters.

The optical system 1 further comprises a flip switch 74 as a control element. By operating the flip switch 74, the optical system 1 is switchable into a first and a second operating mode. In the first operating mode, the controller 4 is configured so that by using the foot pedal 70 and the knob 73, operating parameters of the OCT system 2 are adjustable. In the second operating mode, the controller 4 is configured so that by using the foot pedal 70 and the knob 73, operating parameters of the microscope system 3 are adjustable.

By way of example, in the first operating mode, by using the foot pedal 70, a zoom magnification of the zoom system 50 can be adjusted and by using the knob 73, the object plane distance of the object plane can be adjusted. In the first operation mode, this allows the surgeon to adjust two different operating parameters of the microscope system by using both control elements.

In the second operating mode, by using the foot pedal 70, the beam waist diameter of the measurement beam is adjusted and by using the knob 73, the axial beam waist position of the measurement beam 9 is adjusted. By using both control elements the second operating mode, this allows the surgeon to adjust two different operating parameters of the OCT system 2.

By virtue of the operating elements and by providing the possibility of switching the control elements into the first or into the second operating mode, the surgeon can switch between the operation of the microscope system and the operation of the OCT system in an efficient way and thereby the surgeon can use the optical system in an efficient manner when conducting surgical procedures.

While the disclosure has been described with respect to certain exemplary embodiments thereof, it is evident that many alternatives, modifications and variations will be apparent to those skilled in the art. Accordingly, the exemplary embodiments of the disclosure set forth herein are intended to be illustrative and not limiting in any way. Various changes may be made without departing from the spirit and scope of the present disclosure as defined in the following claims.

The invention claimed is:

1. An optical system for inspecting an eye comprising:
a microscopy system for generating an image of an object region in an image plane;
wherein the microscopy system comprises a zoom system for varying an imaging magnification of the generation of the image through a variation of a zoom magnification of the zoom system;
an OCT system, which is configured to generate a measurement beam, which is incident on the object region in a converging manner to form a measurement focus which comprises a beam waist;
wherein the optical system comprises a controller for controlling a beam waist diameter of the beam waist and for controlling the zoom magnification;
wherein the controller is configured for a coupled control of the beam waist diameter and the zoom magnification according to a predefined dependency between the beam waist diameter and the zoom magnification; and
wherein the controller is configured for selectively activating and deactivating the coupled control of the beam waist diameter and the zoom magnification.

2. The optical system according to claim 1, wherein the controller is further configured for a coupled control of the beam waist diameter and a length of an axial measurement range of the OCT system according to a predefined dependency between the beam waist diameter and the length of the axial measurement range.

3. An optical system for inspecting an eye, the optical system comprising:
an OCT system which is configured to generate a measurement beam, which is incident on an object region in a converging manner to form a measurement focus which comprises a beam waist;
wherein the OCT system comprises a scanning system, an objective lens, and a beam expander, wherein the beam expander is configured for a controllable beam expansion of the measurement beam, wherein the scanning system, the objective lens and the beam expander are disposed in the measurement beam;
wherein the beam expander is disposed along the measurement beam between the scanning system and the objective lens and generates an intermediate focus between the scanning system and the objective lens;
wherein the OCT system is configured to generate different values of a beam waist diameter of the beam waist by means of controlling the controllable beam expansion; and
wherein at the different values of the beam waist diameter, an axial beam waist position of the beam waist is substantially identical.

4. The optical system according to claim 3, wherein:
at each of the different values of the beam waist diameter, a position of an object-side focal plane of the beam expander is substantially identical; or
at each of the different values of the beam waist diameter, the beam expander is an afocal system.

5. The optical system according to claim 3 further comprising a microscopy system, which is configured for generating an image of an object region in an image plane, wherein the object region is located in an object plane, which is optically conjugate to the image plane;
    wherein the microscope system is configured to generate an observation channel for generating the image, wherein the observation channel traverses the objective lens;
    wherein at the different values of the beam waist diameter, the beam waist is located outside of the object plane.

6. The optical system according to claim 3, wherein a portion or all of the optically effective surfaces of the beam expander generate a controllably variable focal length for focusing the measurement beam to the intermediate focus.

7. The optical system according claim 6, wherein the beam expander is configured so that at different values of the variable focal length, a position of the intermediate focus along an axis of the measurement beam is substantially identical.

8. The optical system according to claim 3, wherein the beam expander comprises:
    a plurality of controllably movable optical units;
    wherein for adjusting the different values of the beam waist diameter, the movable optical units move relative to each other.

9. The optical system according to claim 3, wherein the beam expander comprises:
    a first controllably movable optical unit, which comprises a negative refractive power.

10. The optical system, according to claim 9, wherein the beam expander further comprises:
    a second controllably movable optical unit, which comprises a positive refractive power;
    wherein the first and the second movable optical units are moved relative to each other when performing a variation of the beam expansion.

11. The optical system according to claim 10, wherein the first and the second optical units are disposed upstream of the intermediate focus, relative to a light direction of the measurement beam toward the object.

12. The optical system according to claim 3, further comprising a third optical unit, which comprises a negative refractive power and which is disposed downstream of a first and/or a second movable optical unit, relative to a light direction of the measurement beam toward the object.

13. The optical system according to claim 12, wherein the third optical unit is arranged upstream of the intermediate focus relative to the light direction of the measurement beam toward the object.

14. The optical system according to claim 3, wherein the beam expander is configured so that a position of an object-side focal plane of the beam expander is controllably variable.

15. The optical system according to claim 3, wherein the different values of the beam waist diameter are caused by the controlling of the controllable beam expansion.

16. An optical system, comprising:
    an OCT system, which is configured to generate a measurement beam, which is incident on the object region in a converging manner to generate a measurement focus, which comprises a beam waist;
    wherein the OCT system comprises a scanning system, an objective lens and a beam expander, wherein the beam expander is configured for a controllable beam expansion of the measurement beam, wherein the scanning system, the objective lens and the beam expander are disposed in the measurement beam;
    wherein the beam expander is disposed along the measurement beam between the scanning system and the objective lens and generates an intermediate focus of the measurement beam between the scanning system and the objective lens; and
    wherein a portion or all of the optically effective surfaces of the beam expander generate a controllably variable focal length for focusing the measurement beam to the intermediate focus.

17. The optical system according claim 16, wherein the beam expander is configured so that at different values of the variable focal length, a position of the intermediate focus along an axis of the measurement beam is substantially identical.

18. The optical system according to claim 16, wherein the beam expander is configured so that:
    at different values of the variable focal length, a position of an object-side focal plane of the beam expander is substantially identical; or
    at different values of the variable focal length, the beam expander is an afocal system.

19. The optical system according to claim 16, wherein the beam expander comprises:
    a first controllably movable optical unit, which comprises a negative refractive power.

20. The optical system, according to claim 19, wherein the beam expander further comprises:
    a second controllably movable optical unit, which comprises a positive refractive power; and
    wherein the first and the second movable optical units are moved relative to each other when performing a variation of the beam expansion.

21. The optical system according to claim 20, wherein the first and the second optical units are disposed upstream of the intermediate focus, relative to a light direction of the measurement beam toward the object.

22. The optical system according to claim 16, further comprising a third optical unit, which comprises a negative refractive power and which is disposed downstream of a first and/or a second movable optical unit, relative to a light direction of the measurement beam toward the object.

23. The optical system according to claim 22, wherein the third optical unit is arranged upstream of the intermediate focus relative to the light direction of the measurement beam toward the object.

24. The optical system according to claim 16, wherein the beam expander is configured so that a position of an object-side focal plane of the beam expander is controllably variable.

* * * * *

UNITED STATES PATENT AND TRADEMARK OFFICE
CERTIFICATE OF CORRECTION

PATENT NO. : 9,662,010 B2
APPLICATION NO. : 14/859700
DATED : May 30, 2017
INVENTOR(S) : Christoph Hauger et al.

It is certified that error appears in the above-identified patent and that said Letters Patent is hereby corrected as shown below:

In the Specification

Column 3, Line 2, "may configured" should read --may be configured--.

Column 5, Line 24, "can achieved" should read --can be achieved--.

Column 5, Line 31, "bef" should read --be--.

Column 13, Line 22, "item" should read --Item--.

Column 13, Line 28, "item" should read --Item--.

Column 18, Line 21, "Theses" should read --These--.

Column 19, Line 50, "in" should read --is--.

Column 20, Line 42, "in to" should read --into--.

Column 20, Line 51, "its" should read --it--.

Column 23, Line 4, "component is needs" should read --component needs--.

Column 23, Line 46, "mall" should read --small--.

In the Claims

Column 27, Line 16, "according claim" should read --according to claim--.

Signed and Sealed this
Twenty-ninth Day of August, 2017

Joseph Matal
*Performing the Functions and Duties of the
Under Secretary of Commerce for Intellectual Property and
Director of the United States Patent and Trademark Office*